(12) United States Patent
Sotoaka et al.

(10) Patent No.: US 7,892,404 B2
(45) Date of Patent: Feb. 22, 2011

(54) METHOD FOR OXIDIZING SUBSTANCE AND OXIDATION APPARATUS THEREFOR

(75) Inventors: Ryuji Sotoaka, Chiba (JP); Yoshiya Kimura, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 1128 days.

(21) Appl. No.: 11/597,250

(22) PCT Filed: May 18, 2005

(86) PCT No.: PCT/JP2005/009077
§ 371 (c)(1),
(2), (4) Date: Nov. 20, 2006

(87) PCT Pub. No.: WO2005/113134
PCT Pub. Date: Dec. 1, 2005

(65) Prior Publication Data
US 2007/0215454 A1   Sep. 20, 2007

(30) Foreign Application Priority Data
May 21, 2004 (JP) .............................. 2004-151193

(51) Int. Cl.
*C07C 1/00* (2006.01)
*C01B 13/00* (2006.01)
*C01D 1/00* (2006.01)

(52) U.S. Cl. .............................. 204/157.15; 204/157.5; 204/157.51

(58) Field of Classification Search ............ 204/157.15, 204/157.5, 157.51
See application file for complete search history.

(56) References Cited

U.S. PATENT DOCUMENTS

| | | | | |
|---|---|---|---|---|
| 3,458,418 A | * | 7/1969 | Beckmann | 204/157.15 |
| 4,474,829 A | * | 10/1984 | Peters | 438/765 |
| 6,043,294 A | * | 3/2000 | Hed | 522/1 |
| 2009/0114619 A1 | * | 5/2009 | Sotoaka et al. | 216/48 |

FOREIGN PATENT DOCUMENTS

CA    2188922    11/1994

(Continued)

OTHER PUBLICATIONS

Broszkiewicz et al., "Reactions of Hydroxyl Radicals with Acetylacetone in Aqueous Solution. A Pulse Radiolysis and Electron Spin Resonance Study", Zeitschrift fuer Naturforschung, Teil B: Anorganische Chemie, Organische Chemie (no month, 1982), vol. 37B, No. 3, pp. 368-375.*

(Continued)

*Primary Examiner* — Edna Wong
(74) *Attorney, Agent, or Firm* — Antonelli, Terry, Stout & Kraus, LLP.

(57) ABSTRACT

The present invention provides a method of oxidizing a substance in a liquid containing nitrous oxide ($N_2O$) and an oxidation apparatus therefor. In this method, oxidation of a substance is conducted by allowing a substance to be present in a solution containing nitrous oxide ($N_2O$) and irradiating the solution with light including a wavelength of at least 240 nm or less.

20 Claims, 8 Drawing Sheets

FOREIGN PATENT DOCUMENTS

| | | |
|---|---|---|
| DE | 43 17 939 A1 | 11/1994 |
| JP | 60-063373 | 4/1985 |
| JP | 60063373 A * | 4/1985 |
| JP | 1-233727 | 9/1989 |
| JP | 04-036456 | 2/1992 |
| JP | 09-008037 | 1/1997 |

OTHER PUBLICATIONS

Dainton et al., "Photochemistry of Aqueous Solutions of Potassium Iodide Containing N2O", Bulletin des Societes Chimiques Belges (no month, 1962), vol. 71, pp. 801-802.*

Supplementary European Search Report dated Jul. 1, 2008, for Application No. 05740974.0-2104/1749570 PCT/JP2005009077.

* cited by examiner

FIGURE 12
CONVENTIONAL

(a)

(b)

(c)

(d)

(e)

(f)

METHOD FOR OXIDIZING SUBSTANCE AND OXIDATION APPARATUS THEREFOR

TECHNICAL FIELD

The present invention relates to a method of oxidizing a substance and to a substance oxidation apparatus, and more specifically to oxidation of a substance in a liquid employing nitrous oxide ($N_2O$)-dissolved water.

BACKGROUND ART

Production of an industrial product through oxidation of an organic compound employs a method involving mixing an oxygen-containing substance referred to as an oxidant and an organic compound and conducting an oxidation reaction by using a catalyst, heat, or the like.

For example, industrial production of adipic acid as a raw material for nylon employs a method (nitric acid oxidation) of oxidizing cyclohexanone or cyclohexanol as a raw material by using a large amount of nitric acid. This method employs nitric acid, which is a strong acid, as an oxidant, and thus has problems such as an increased cost for a measure against corrosion of an apparatus and an increased cost for reduction of risks in production.

Industrial production of terephthalic acid as a raw material for a polyester employs a method (air oxidation) of oxidizing paraxylene as a raw material by using oxygen in air. This method employs cobalt, manganese, and a boron compound as catalysts, and thus has problems such as an increased cost for a measure against corrosion due to boron and an increased cost for reduction of an environmental load due to boron.

An example of a method of oxidizing a substance such as a silicon wafer is a method of bringing a substrate into contact with water containing an oxidizing substance dissolved therein. Examples of water containing an oxidizing substance dissolved therein include a hydrogen peroxide solution and ozone water.

The hydrogen peroxide solution is used for bleaching of paper or pulp, washing of a semiconductor, sterilization, disinfection, and the like by utilizing the oxidizing power thereof. The ozone water is used for sterilization of water supply and sewage system and sterilization of food and tableware, and is recently used for washing of a semiconductor and the like.

The hydrogen peroxide solution is relatively stable, and hydrogen peroxide remains for a relatively long period of time in waste water obtained after the hydrogen peroxide solution is used for various applications. Thus, the waste water of the hydrogen peroxide solution requires decomposition treatment for reducing an environmental load, and industrial use of a large amount of the hydrogen peroxide solution or the like causes a problem of an increased cost required for the decomposition treatment.

Meanwhile, the ozone water is relatively unstable and therefore decomposes spontaneously in a relatively short period of time. However, the ozone water is toxic to human body even in a low concentration and provides a heavy load on a material used for a piping system or the like, so that the ozone water requires decomposition treatment. Thus, the ozone water has a problem of causing a treatment cost. The ozone water is relatively unstable, and storage of the ozone water while maintaining the oxidizing power thereof for a long period of time is substantially impossible. That is, the ozone water is inconvenient in that a method of using a required amount of ozone water at a required time from a large amount of stored ozone water is impossible. Further, stable supply of ozone water after start of an ozone water production apparatus in a stopped state requires a certain period of time for start-up of the apparatus. In the case where intermittent use of ozone water is supposedly desired, an operating state of the ozone water production apparatus must be maintained at all times even during time requiring no ozone water if an apparatus start-up time is longer than time requiring no ozone water. Thus, a useless raw material cost or a useless running cost is inevitably caused.

Another example of the method of oxidizing a substance is a method employing a photocatalyst. The photocatalyst is a substance which exhibits a catalytic action under irradiation of light, and a typical example of the photocatalyst is titanium dioxide having an anatase crystal structure. Titanium dioxide exhibits an oxidizing action under irradiation of light having a wavelength shorter than about 380 nm. In the presence of a target substance to be oxidized in a gas phase, titanium dioxide is allowed to be present in the gas phase, and the gas phase is irradiated with light for oxidation of the target substance. In the presence of a target substance to be oxidized in water, titanium dioxide is allowed to be present in water, and water is irradiated with light for oxidation of the target substance.

Titanium dioxide is used for deodorization and decomposition of a malodorous component such as ammonia or formaldehyde, sterilization and purification of drink water or waste water, and the like by utilizing its oxidizing power as a photocatalyst. Titanium dioxide is often used in a thin film form fixed on an appropriate substrate surface for easy handling and basically exhibits an oxidizing action on a substance adsorbed on a surface of titanium dioxide alone. Thus, diffusion and adsorption of a substance to be oxidized itself from and to the surface of titanium dioxide in a gas phase or water control rate of oxidation, and use of titanium dioxide has a problem of a relatively slow oxidation rate.

In use of titanium dioxide in water, a water molecule adsorbed on the surface of titanium dioxide is oxidized to generate a hydroxy radial having oxidizing power. The hydroxy radical has a very short life and exists in adjacent to titanium dioxide very closely. Thus, no substantial oxidizing action of the hydroxy radical derived from diffusion of the hydroxy radical can be confirmed in water distant from titanium dioxide. In this way, the hydroxy radical differs from the hydrogen peroxide solution or ozone water and has a problem in that even when a solid substance exhibiting no solubility in water such as a semiconductor substrate is immersed in water containing titanium dioxide, a surface of the solid substance cannot be oxidized in the presence or absence photoirradiation. In the case where an attempt of increasing an oxidation rate is made by dispersing titanium dioxide in a form of fine powder in water, this case has a problem in that separation and recovery of titanium dioxide after oxidation treatment involves difficulties.

There is proposed an oxidation method employing nitrous oxide. Nitrous oxide ($N_2O$) is a stable gas under normal temperature and normal pressure and is not decomposed by visible light. For example, Non-patent Document 1 describes properties of nitrous oxide. Nitrous oxide is known to decompose into a nitrogen molecule ($N_2$) and atomic oxygen (O) under irradiation of light having a wavelength shorter than 240 nm. Non-patent Document 2 describes this phenomenon, for example.

Many researches have been conducted regarding oxidation of a target substance by using atomic oxygen (O) generated in a gas phase. For example, Non-patent Document 3 describes oxidation of a surface of an Si wafer.

Patent Document 1 discloses an invention involving: removing a natural oxide film on a surface of a silicon substrate with a diluted hydrofluoric acid solution; heating the silicon substrate to about 300° C.; brining an ultra pure oxygen gas into contact with the silicon substrate to form a silicon oxide film of about an intermolecular distance, and heating the silicon substrate to 900° C. to form an oxide film having a predetermined thickness. Oxidation of the silicon substrate can be conducted by using a solution containing oxygen and/or a molecule containing oxygen. The solution to be used may be a solution containing oxygen dissolved therein, a solution containing ozone dissolved therein, a hydrogen peroxide solution, a sulfuric acid/hydrogen peroxide aqueous solution, a hydrochloric acid/hydrogen peroxide aqueous solution, or an ammonia/hydrogen peroxide aqueous solution (see paragraph 0013 of Patent Document 1).

Patent Document 2 discloses a method of using nitrous oxide and forming a natural oxide on a surface of a semiconductor substrate with an oxygen atom generated from nitrous oxide. Formation of the oxide is conducted in a gas phase under pressure less than an atmospheric pressure.

Production of electronic components employs a technique of oxidation (hereinafter, referred to as local oxidation) and insulating a selected region on a conductive material for various purposes. Further, there is realized a technique of working a substrate by forming an oxide film layer having high chemical resistance through local oxidation, and using the oxide film layer as a mask for dissolving and removing a non-oxidized region with a chemical. Production of an ornament widely employs a technique of forming an oxidized region having a different color from that of a non-oxidized region or an oxidized region having improved coloring property than that of a non-oxidized region on a substrate surface as a pattern for obtaining an ornament with a very aesthetic appearance.

Figure 12:
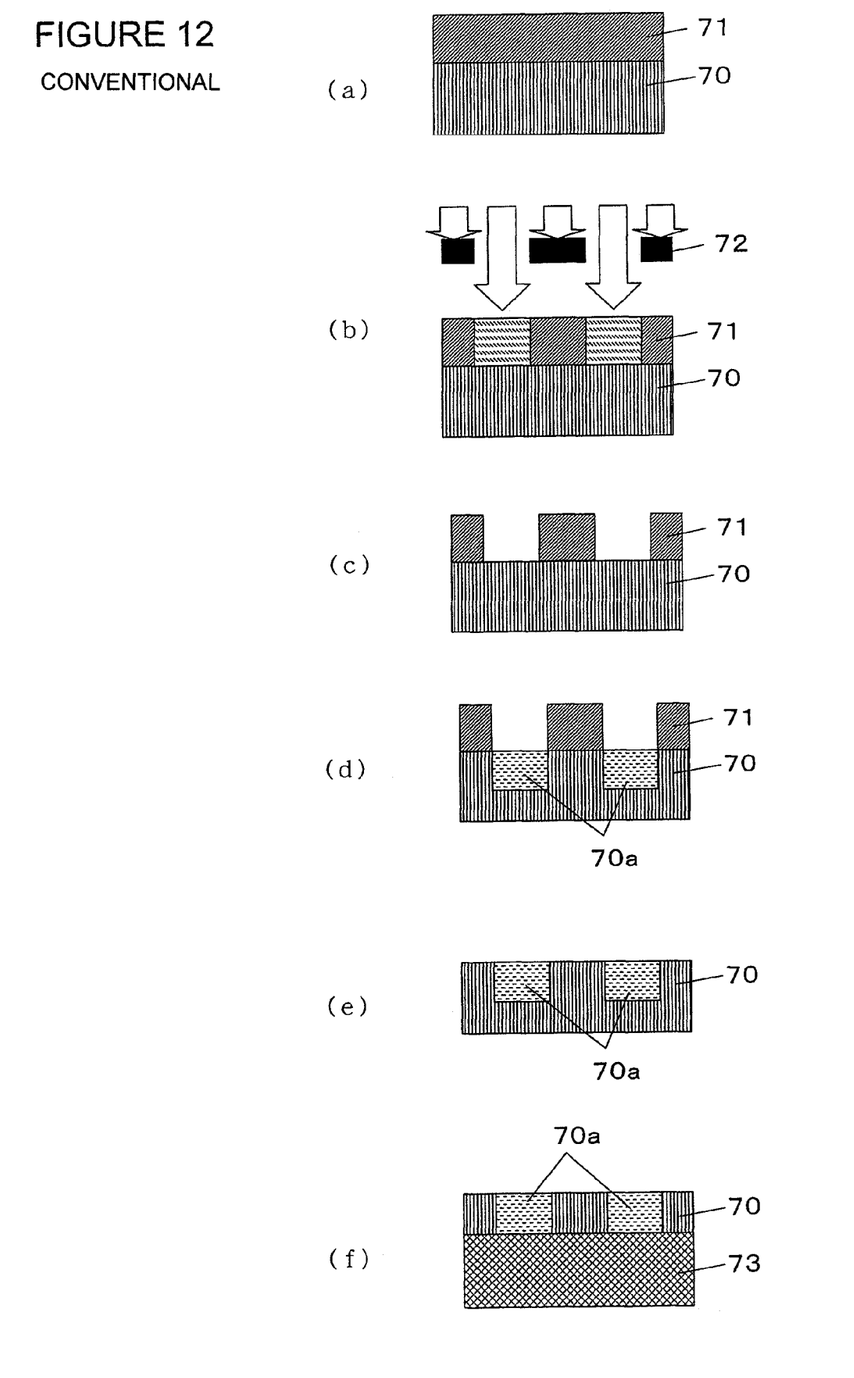
FIG. 12 A diagram showing a conventional method of local oxidation employing a photolithography step.

The local oxidized region is conventionally formed by a method involving: forming a resist pattern or a pattern of an oxidation resistant material in a photolithography step; using the pattern as a mask; and oxidizing a region not covered with the mask. Alternatively, the local oxidized region is conventionally formed by a method involving: forming an oxide layer on a substrate surface in advance; forming a resist pattern in a photolithography step; using the pattern as an etching mask; and dissolving and removing the oxide layer in a region not covered with the mask to obtain the oxide layer in a region covered and protected by the resist alone. FIG. 12 shows the local oxidation method employing the photolithography step conventionally used and employing the resist described above.

First, as shown in FIG. 12(a), a photoresist layer 71 is formed on a substrate 70 to be subjected to local oxidation by a spin coating method or roller coating method of a liquid resist, a laminating method of a dry film resist, or the like conventionally and often used.

Next, as shown in FIG. 12(b), the photoresist layer 71 is exposed to light through a mask (reticle) 72 having a predetermined pattern and then developed, to thereby form the photoresist layer 71 into a mask pattern having a predetermined shape as shown in FIG. 12(c).

Then, as shown in FIG. 12(d), a region on the substrate 70 corresponding to an opened part of the photoresist layer 71 is selectively oxidized, by using the photoresist layer 71 having a predetermined shape as a mask, by a wet chemical oxidation method employing a solution containing an oxidant such as a hydrogen peroxide solution or ozone water, an anodic oxidation method in an electrolytic solution, a dry oxidation method such as oxygen ion implantation or heat oxidation employing a quartz reaction tube, or the like, to thereby form an oxidized region 70a.

After local oxidation, the resist layer 71 is removed through dry ash treatment employing plasma, wet treatment employing a resist removing liquid, or the like, to thereby obtain the substrate 70 having the desired oxidized region 70a formed thereon as shown in FIG. 12(e).

The oxidized region 70a may be formed to float (island) on the surface of the substrate 70 as shown in FIG. 12(e), or may be formed to reach a primary layer 73 as shown in FIG. 12(f) depending on the intended use.

For example, production of a semiconductor apparatus generally employs a technique of local oxidation of silicon (LOCOS) involving: forming a mask pattern of silicon nitride which is an oxidation resistant material on a silicon wafer in a photolithography step; and locally oxidizing and insulating silicon in a region not covered with silicon nitride by a dry oxidation method.

Patent Document 3 discloses a technique of forming a resist pattern on a metal thin film of aluminum, tantalum, or the like in a photolithography step and locally oxidizing and insulating the metal thin film in a region not covered with the resist pattern by an anodic oxidation method for dielectric isolation of the metal thin film in a matrix form in production of an active matrix-type reflective liquid crystal display apparatus.

Patent Document 4 discloses a technique of forming a resist pattern on a conductive material (such as iron, zinc, aluminum, aluminum alloy, titanium, tantalum, copper, copper alloy, silicon, silicon alloy, silver, zirconium, tungsten, chromium, or molybdenum) in a photolithography step, and locally oxidizing and insulating the conductive material in a region not covered with the resist pattern by an anodic oxidation method, a heat oxidation method, or an ion injection method for insulation treatment of a part of a leading electrode layer for leading a signal from a thin film magneto-resistance element excluding a leading electrode shape to form a pair of leading electrode parts as insulated parts in production of a thin film magneto-resistance effective head to be used for a magnetic information recording apparatus such as a hard disk.

Patent Document 5 discloses a technique of providing an oxide film on a surface of a silicon wafer in advance, forming a resist pattern in a photolithography step, removing the oxide film in a region not covered with the resist pattern with a hydrofluoric acid buffer solution, removing the resist in a mixed system of sulfuric acid and a hydrogen peroxide solution to form a pattern of a silicon oxide film, and etching a region not covered with the silicon oxide film with an alkali solution by using the silicon oxide film pattern as a mask in micromachining for producing a precision machine component, a microsensor, or the like employing a silicon wafer such as a semiconductor pressure sensor or an inkjet printer head.

Patent Document 6 discloses a technique of providing an oxide film on a surface of a substrate (such as aluminum, copper, manganese, silicon, magnesium, or zinc) in advance, forming a resist pattern in a photolithography step, removing the oxide film in a region not covered with the resist pattern with an alkali solution, and removing the resist to form an oxide film pattern in a defined region in a method of producing an ornament.

Patent Document 1: JP-B 3210370
Patent Document 2: JP-B 4-36456
Patent Document 3: JP-A 10-268359
Patent Document 4: JP-A 6-338035
Patent Document 5: JP-B 3525612
Patent Document 6: JP-A 2005-15898

Non-patent Document 1: Naotoshi Yamanouchi, Mitsuo Takeda, "Nitrous oxide", High Pressure Gas, Vol. 13 No. 3 (1976) p 105-111

Non-patent Document 2: "Photochemical Reaction in Gas Phase", edited by Chemical Society of Japan, Kagaku Sousetsu Muki-Hikari Kagaku Gakkai Shuppan Center, No. 39, (1983) p 14-38

Non-patent Document 3: K. Uno, A. Namiki, S. Zaima, T. Nakamura, N. Ohtake, "XPS Study of the Oxidation Process of Si(111) via Photochemical Decomposition of N2O by an DV Excimer Laser", Surface Science, 193(1988), p 321-335

DISCLOSURE OF THE INVENTION

However, the above-mentioned conventional methods of oxidizing a silicon substrate or the like have the following problems. Patent Document 1 describes the invention employing a solution containing ozone dissolved therein or a hydrogen peroxide solution as a solution used for oxidation of the silicon substrate. Thus, waste water obtained after the solution is used must be subjected to decomposition treatment, thereby causing cost increase.

Patent Document 2 describes the oxidation method in a gas phase by using nitrous oxide, and handling of the gas involves difficulties. Further, the method requires a sealing device such as a treatment chamber for suppressing generation of ozone, and a temperature inside the treatment chamber must be increased as required. Thus, a production cost of oxidation with nitrous oxide increases.

Patent Documents 3 to 6 describe the techniques each requiring a photolithography step consisting of many steps such as a resist layer forming (resist applying) step, a light exposure step, a development step, and a removing step for realizing local oxidation of a substrate. The steps employ different apparatuses and require much labor and effort for handling, control, and maintenance of the apparatuses. The resist forming step involves vaporization of an organic solvent during curing of the resist, and the developing step generally employs large amounts of a strong alkali solution and an organic solvent. Further, etching of an oxide film layer employs chemicals such as a strong alkali and hydrofluoric acid. Thus, the techniques require maintenance in chemical storage, safety in chemical use, and treatment of waste water after use, thereby causing cost increase.

An object of the present invention is to provide a method of oxidizing a substance solving the above-mentioned conventional problems, providing a low environmental load, involving easily handling, and capable of oxidizing a substance at a relatively low cost, and an oxidation apparatus therefor.

The inventors of the present invention have conducted intensive studies and have found a method of solving the above-mentioned conventional problems at once by using a method of irradiating nitrous oxide dissolved in water with light. That is, the present invention provides a method of oxidizing a substance by using a solution by bringing a substance into contact with a solution containing nitrous oxide ($N_2O$) and irradiating the solution with light having a wavelength of at least 240 nm or less for oxidation of the substance, and a substance oxidation apparatus.

According to the present invention, oxidation of a substance can be conducted by bringing a substance into contact with a solution containing nitrous oxide, and irradiating the solution with light having a wavelength of 240 nm or less to dissociate nitrous oxide and generate atomic oxygen (O) having strong oxidizing power. A life of atomic oxygen (O) is very short and is about nano seconds. A possibility of atomic oxygen (O) dissociated under photoirradiation to transfer to and react with a substrate in a region not irradiated with light is very low. A defined region is irradiated with light, to thereby allow reaction of the substrate in the defined region with atomic oxygen (O) dissociated under photoirradiation for oxidation. This phenomenon indicates that an oxidized region having a desired shape can be formed on a substrate by using a mask similar to that used for semiconductor production. Further, a selected region alone of a target substance may not be subjected to oxidation by arranging a mask having no region allowing light transmittance on the selected region of the target substance and shielding light to the selected region alone of the target substance. For dissociation of nitrous oxide under irradiation of UV light of 240 nm or less in a gas phase, an ozone gas ($O_3$) which is toxic to human body or the environment generates in the presence of oxygen in air, but generation of the ozone gas can be suppressed in a liquid. Handling of nitrous oxide as a gas requires control of gas leak or the like, and handling of nitrous oxide is not necessarily easy. However, handling of water containing nitrous oxide dissolved therein is very easy. Difference in handling ease between a gas and a solution containing a dissolved gas is generally known. For example, a hydrogen chloride gas is a strongly irritant substance, irritates a nasal or ocular membrane, and is fatal to humans under exposure of the gas of 1,000 ppm or more for few minutes. Meanwhile, hydrochloric acid as an aqueous solution of hydrogen chloride is commercially available as a solution having a concentration of about 37% and is widely used in applications such as dissolving of a metal and a production material for a dye, a fragrance, a medicine, an agricultural chemical, or the like. Further, generation of a toxic by-product upon oxidation is very little, and hydrochloric acid basically requires no decomposition treatment of waste water as a hydrogen peroxide aqueous solution or the like, to thereby reduce an environmental load and significantly reduce a treatment cost. Irradiation of the solution with light having a wavelength of at least 240 nm or less while a light irradiation region is controlled allows oxidation of the selected region of the substrate and allows oxidation of a desired region without a photolithography step employing a complex resist.

BRIEF DESCRIPTION OF THE DRAWINGS

FIG. 4 A graph showing a relationship between time and absorbance of a methylene blue aqueous solution at 665 nm obtained by using the experimental apparatus of FIG. 1 in the case where a high pressure mercury lamp is not turned on.

DESCRIPTION OF SYMBOLS 1, 2: OXIDATION APPARATUS
10, 40, 45: CONTAINER
30, 60, 65: AQUEOUS SOLUTION
42, 43: SUPPORT OF SILICON WAFER
20: HIGH PRESSURE MERCURY LAMP
50: LOW PRESSURE MERCURY LAMP
55: OZONE-LESS HIGH PRESSURE MERCURY LAMP
56: LIGHT SHIELDING PLATE
70: SUBSTRATE
70a: OXIDIZED REGION SELECTED ON SUBSTRATE
71: RESIST LAYER
72: MASK (RETICLE)
73: PRIMARY LAYER

BEST MODE FOR CARRYING OUT THE INVENTION

A method of oxidizing a substance according to the present invention involves allowing a target substance to be present in an aqueous solution containing nitrous oxide ($N_2O$) and irradiating the aqueous solution with light having a wavelength of at least 240 nm or less to dissociate $N_2O$ for oxidation of the target substance. Hereinafter, the oxidation method will be described in detail.

Oxidation of the target substance requires some oxidation active species and the target substance to be present in the same system. In general, various oxidation active species are present, and examples thereof include hydrogen peroxide ($H_2O_2$), ozone ($O_3$), superoxide ($O_2^-$), singlet oxygen ($^1O_2$), a hydroxy radical (.OH), and atomic oxygen (O). Those species each have different oxidizing power. For oxidation of the target substance, it is obviously advantageous that oxidizing power of the oxidation active species be high. Thus, the inventors of the present invention have conducted studies regarding a method of oxidizing a target substance by using atomic oxygen (O), which is an oxidation active species having very high oxidizing power.

However, no studies have been conducted regarding a method of oxidizing a target substance by irradiating nitrous oxide dissolved in water with light, generating atomic oxygen (O) in the water, and allowing the target substance to be present in the water. Further, no detailed findings have been reported regarding effectiveness of this method.

With a special exception, nitrous oxide is not dissociated by energy transferred from energy of light received by a substance present in a vicinity of nitrous oxide. The special exception refers to photosensitized decomposition of mercury in which: a mercury vapor is allowed to be present in a gas phase containing nitrous oxide; the gas phase is irradiated with light to convert mercury into an excited state; and energy is provided to nitrous oxide from mercury in the excited state for dissociation of nitrous oxide. The special exception is described in R. Simonaitis, Raymond I. Greenberg, Julian Heicklen, "The Photolysis of $N_2O$ at 2,139 Å and 1,849 Å", International Journal of Chemical Kinetics, Vol. 4 (1972), pp. 497-512.

That is, in general, dissociation of nitrous oxide is a phenomenon caused by an $N_2O$ molecule directly receiving energy of light, and the phenomenon basically occurs in a gas phase or water. In this way, the inventors of the present invention have reached an idea that dissociation of nitrous oxide can be caused under irradiation of light even in water and that oxidation of a target substance can be realized by atomic oxygen (O) caused by the dissociation. As described above, nitrous oxide absorbs no light with $\square$>240 nm, and for dissociation of $N_2O$ into $N_2$ and O, light having a wavelength of $\square$<240 nm is desired.

British Journal of Anaesthesia, 1972, 44(4), 310 reports absorption spectra of nitrous oxide in a gas phase and nitrous oxide in water, and the report describes that a maximum absorbance is at a wavelength of 190 nm.

Meanwhile, for appropriate decomposition of nitrous oxide dissolved in water, it is desired that light be not absorbed by water and most of light be absorbed by nitrous oxide. Light absorption by water ($H_2O$) is known to have a peak at 167 nm, and thus light having a wavelength longer than at least the wavelength of the peak is desirably irradiated. From experimental results disclosed in Examples described below, light having a wavelength of 173 nm or more is desirably irradiated for suppressing light absorption by water.

A concentration of $N_2O$ to be dissolved in water must be 10 ppm or more for obtaining sufficient effects. A high concentration leads to an increased oxidation rate and allows oxidation in a short period of time. However, in consideration of effects of concentration change due to generation of bubbles or dissipation of $N_2O$ into an atmosphere under photoirradiation at an atmospheric pressure, the concentration is preferably 5,000 ppm or less, more preferably 100 ppm to 4,000 ppm, and most preferably 500 ppm to 3,000 ppm.

A temperature of a solution containing nitrous oxide causing oxidation must be 1° C. or higher in consideration of effects of solidification of water. The temperature thereof must be 99° C. or lower in consideration of effects of boiling of water. In consideration of a reduced saturated solubility concentration with increasing temperature and a reduced oxidation rate with reducing temperature of a substance to be oxidized itself, a temperature range is preferably 3° C. to 70° C., and more preferably 5° C. to 60° C.

As a pressure of an atmosphere to be brought into contact with a solution for oxidation, oxidation may be realized at a certain reduced pressure or at a certain increased pressure. However, the pressure is preferably about an atmospheric pressure in consideration of dissipation of nitrous oxide from water due to reduced pressure and dissolving of an atmospheric gas in water due to increased pressure. In the case where an light transmitting member or the like is used to prevent direct contact between the solution and the atmospheric gas, the atmospheric pressure need not be at about an atmospheric pressure.

However, for preventing reduction in luminance due to light absorption by an oxygen molecule in an atmosphere before light emitted from a light source and having a wavelength of 240 nm or less is injected into a solution or preventing generation of ozone, a space between the light source and the solution may be controlled to about an atmospheric pressure with an inert gas. Further, a vacuum region employing a light transmitting member may be arranged in an arbitrary space between the solution and the light source, or the light source itself may be arranged in the solution together with the substance.

According to the present invention, as a solvent for dissolving nitrous oxide, the solvent having an ability of transmitting to light at a wavelength of 240 nm or less is preferred. Preferred examples of the solvent include water, methanol, ethanol, isopropanol, methylcyclohexane, cyclohexane, acetonitrile, hexane, dioxane, glycerine, n-petane, dichloromethane, and the like. Water having a high ability of transmitting light at a wavelength around 190 nm is particularly preferred.

In bringing the solution containing nitrous oxide into contact with the substance for photoirradiation, the substance may be immersed or dissolved in a liquid of the solution containing nitrous oxide. Alternatively, the substance may be brought into contact with droplets of the solution containing nitrous oxide. Further, the solution containing nitrous oxide may be dropped on the substance to be rotated.

According to the present invention, a substance to be subjected to oxidation may be a substance with a characteristic of dissolving into a solution containing nitrous oxide dissolved therein, or a substance with a characteristic of not dissolving into a solution containing nitrous oxide dissolved therein. Examples of the substance having a characteristic of not dissolving into a solution containing nitrous oxide dissolved therein include silicon, aluminum, copper, iron, zinc, titanium, tantalum, silver, zirconium, tungsten, chromium, molybdenum, nickel, hafnium, ruthenium, niobium, yttrium, scandium, neodymium, lanthanum, cerium, cobalt, vanadium, manganese, gallium, germanium, indium, tin, rhodium, palladium, cadmium, antimony, or alloys including them.

In the present invention, upon UV light irradiation of the solution containing nitrous oxide dissolved therein, the substance is oxidized by utilizing atomic oxygen to be generated in the solution. Thus, as a procedure for conducting oxidation, the solution and the substance may be brought into contact with each other, and the whole may be irradiated with UV light. Alternatively, the substance may be irradiated with UV light, and the solution may be brought into contact with the substance, to thereby make such state that the solution is irradiated with UV light. Further, the solution may be irradiated with UV light, and the substance may be brought into contact with the solution.

EXAMPLES

As described above, dissociation of nitrous oxide may be caused even in water under irradiation of light having a wavelength of 240 nm or less, and a substance can be oxidized with atomic oxygen (O) generated through the dissociation. Further, photoirradiation while controlling a light irradiation region allows oxidation of a defined region of a substrate alone. Hereinafter, the present invention will be described in detail by way of examples.

<Oxidation Decomposition of Methylene Blue>

A typical example of a method used for evaluating oxidizing power of a photocatalyst is oxidation decomposition of methylene blue. Methylene blue is blue as an aqueous solution. The blue color disappears and the aqueous solution becomes colorless upon oxidation. For evaluating oxidizing power of a photocatalyst, a change in absorbance of a methylene blue (10 ppm) aqueous solution at 665 nm is generally measured. Reduction of an absorbance of the methylene blue (10 ppm) aqueous solution at 665 nm to about 10% of an initial absorbance generally requires about several tens minutes to several hundreds minutes with a photocatalyst.

Figure 1:
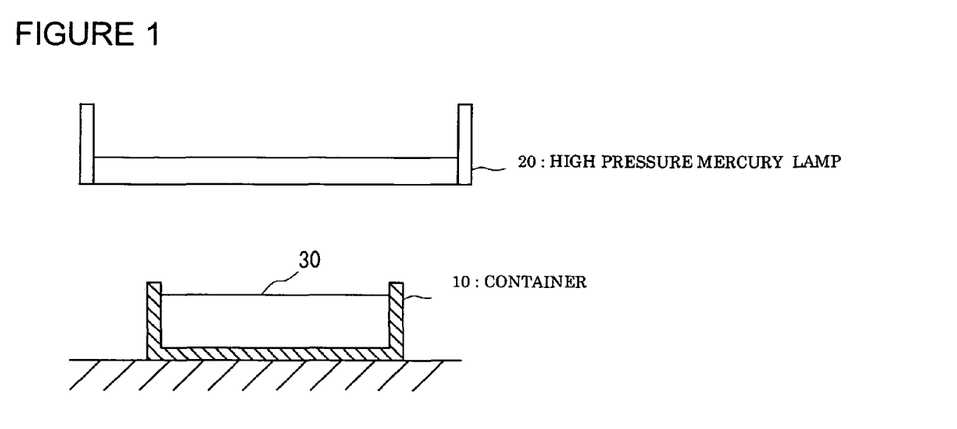
FIG. 1 A schematic diagram of an experimental apparatus for conducting oxidation decomposition of methylene blue.

FIG. 1 is a schematic diagram of an experimental apparatus for conducting oxidation decomposition of methylene blue. The experimental apparatus includes a container 10 having one open surface, and a high pressure mercury lamp 20 arranged directly above the container 10. The high pressure mercury lamp 20 emits light including a wavelength of at least 240 nm or less and has an output of 1,200 W. The high pressure mercury lamp 20 is arranged close to the container 10 such that light of the lamp irradiates all surfaces of the container 10. In the container 10, a methylene blue aqueous solution 30 containing methylene blue (10 ppm) and nitrous oxide dissolved therein is filled.

Figure 2:
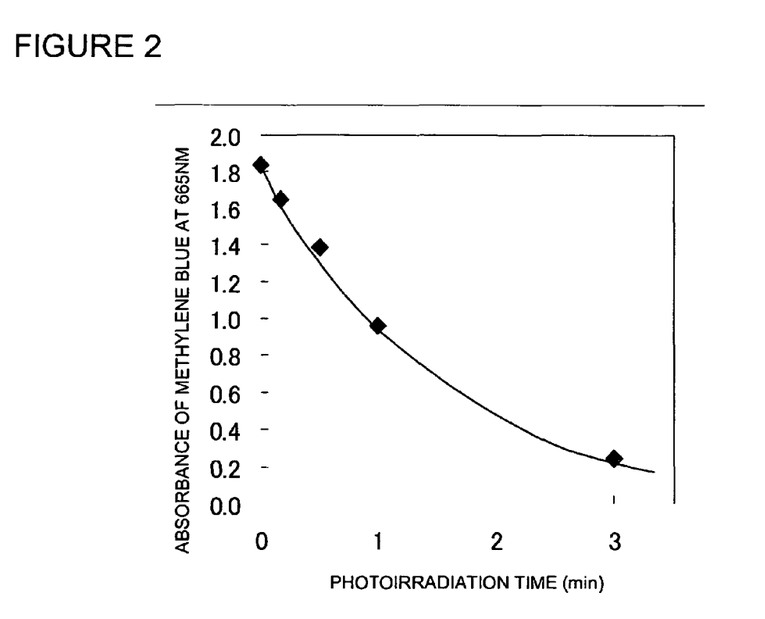
FIG. 2 A graph showing experimental results of oxidation decomposition of methylene blue obtained by using the experimental apparatus of FIG. 1.

FIG. 2 is a graph showing experimental results of oxidation decomposition of methylene blue obtained by using the experimental apparatus shown in FIG. 1. In this case, about 1,000 ppm of nitrous oxide is dissolved. In the graph, a horizontal axis represents a photoirradiation time (min), and a vertical axis represents an absorbance of the methylene blue aqueous solution at 665 nm. Light transmittance (T) is represented by a mathematical expression 1 and an absorbance is represented by a mathematical expression 2, where $I_i$ represents an intensity of light injected into a substance and $I_o$ represents an intensity of light ejected from the substance.

[Math 1]

$$\frac{I_o}{I_i} \times 100 = T \text{ (transmittance)} \quad \text{Mathematical expression 1}$$

[Math 2]

$$-\log\frac{T}{100} = A \text{ (absorbance)} \quad \text{Mathematical expression 2}$$

The graph of FIG. 2 confirmed that about 50% of methylene blue was decomposed with an irradiation time of 1 min, and about 90% of methylene blue was decomposed with an irradiation time of 3 min.

Figure 3:
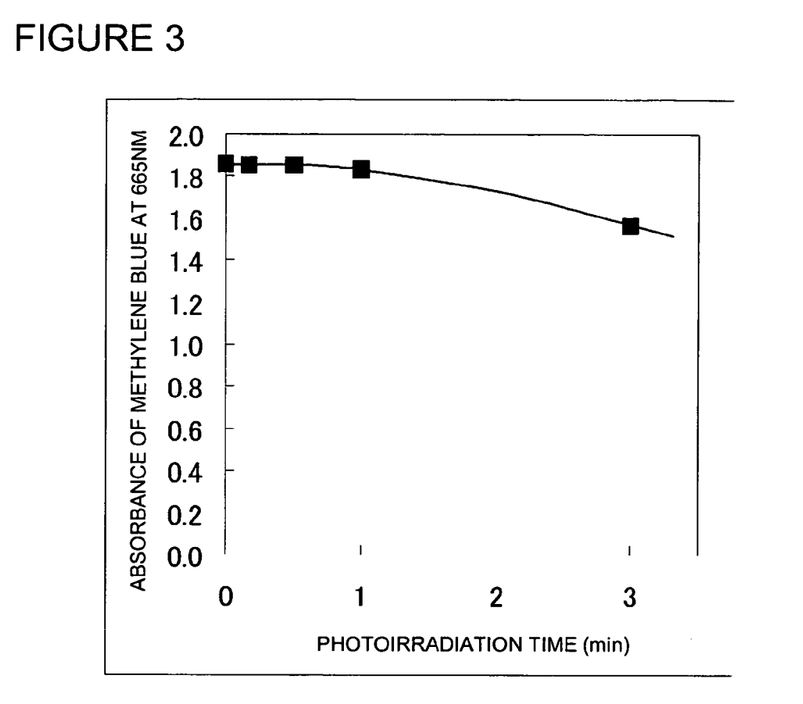
FIG. 3 A graph showing experimental results of oxidation decomposition of methylene blue obtained by using the experimental apparatus of FIG. 1 in the case where an aqueous solution containing methylene blue (10 ppm) and helium (He) dissolved therein is used.

FIG. 3 is a graph showing results of an oxidation decomposition experiment of methylene blue obtained by using the experimental apparatus shown in FIG. 1 in the case where an aqueous solution containing methylene blue (10 ppm) and helium (He, about 16 ppm) dissolved therein is used, and showing a relationship between irradiation time (min) and absorbance of a methylene blue aqueous solution at 665 nm.

Helium (He) is a well known inert gas and is known to absorb no light at 665 nm. For comparison with nitrous oxide-dissolved water, helium (He) was forcibly dissolved in water for removing air components (such as $N_2$, $O_2$, and $CO_2$) dissolved in water to be used. The graph of FIG. 3 revealed that the results differ from the results (shown in FIG. 2) of the case where nitrous oxide-dissolved water was used. Substantially no decomposition was confirmed with an irradiation time of 1 min, and not much methylene blue was decomposed with an irradiation time of 3 min. That is, comparison between FIG. 2 and FIG. 3 confirmed that methylene blue can be oxidized and decomposed under photoirradiation of nitrous oxide.

Figure 4:
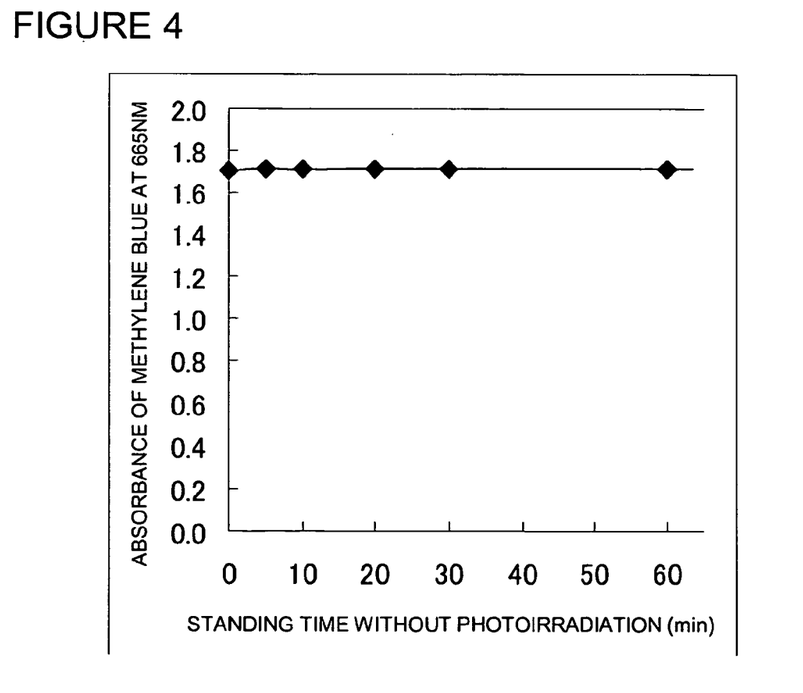

FIG. 4 is a graph showing a relationship between time and absorbance at 665 nm of a methylene blue aqueous solution 30 left standing obtained by using the experimental apparatus shown in FIG. 1 in the case where a high pressure mercury lamp 20 was not turned on. The aqueous solution 30 contains methylene blue and nitrous oxide dissolved therein, but the results confirmed that the absorbance at 665 nm did not change even after the aqueous solution was left standing for 60 min in the absence of irradiation of light having a wavelength of 240 nm or less. That is, comparison between FIG. 2 and FIG. 4 confirmed that methylene blue was not oxidized and decomposed in the absence of photoirradiation of nitrous oxide.

Figure 5:
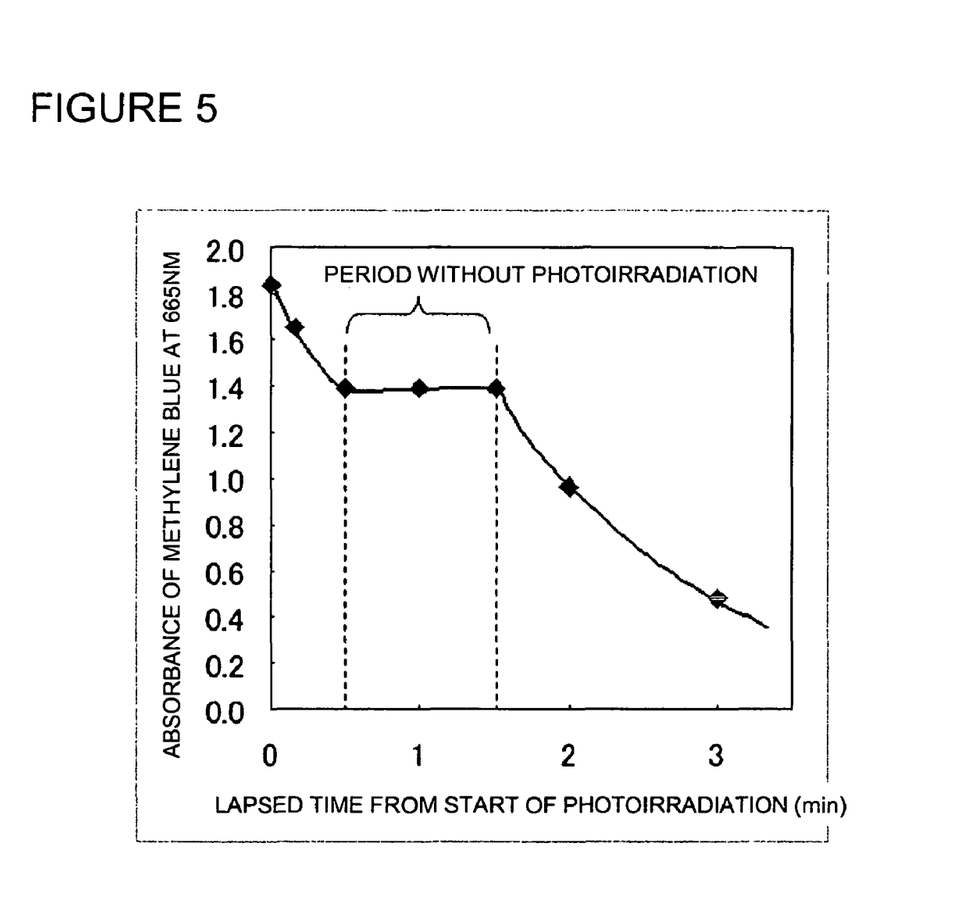
FIG. 5 A graph showing a relationship between time and absorbance of a methylene blue aqueous solution at 665 nm obtained by using the experimental apparatus of FIG. 1 in the case where UV irradiation of the methylene blue aqueous solution is temporarily stopped.

FIG. 5 is a graph showing a change in absorbance of a methylene blue aqueous solution at 665 nm obtained by using the experimental apparatus shown in FIG. 1 in the case where the aqueous solution 30 was irradiated with UV light by the high-pressure mercury lamp 20, the UV light irradiation of the aqueous solution 30 was stopped after 0.5 min, and the aqueous solution 30 was irradiated with UV light again after additional 1 min. The graph of FIG. 5 confirmed that: methylene blue in the aqueous solution was decomposed with start of UV light irradiation; decomposition of methylene blue stopped for 1 min after the UV light irradiation was stopped; and after that, decomposition of methylene blue began with a resumption of the UV light irradiation. In this way, the results confirmed that a substance oxidation time can be controlled by selecting a UV light irradiation time.

The experiments (shown in FIGS. 2 to 5) described above were all conducted at room temperature (about 24° C.). The results confirmed that in the present invention, the substance oxidation time can be controlled by selecting the UV light irradiation time. In the present invention, the life of atomic oxygen is very short, and generation of atomic oxygen stops when the UV light irradiation stops. Thus, stopping of the UV light irradiation substantially indicates stopping of oxidation. In the experiments, the high pressure mercury lamp 20 was used as a light source for dissociating nitrous oxide, but a light source excluding the high pressure mercury lamp can be used as long as the light source emits light having a wavelength of 240 nm or less. The lamp had an output of 1,200 W but may have a different output for realizing oxidation decomposition. In the case where the same lamp is used, an oxidation decomposition rate is generally affected by the output. That is, a small lamp output provides a reduced oxidation decomposition rate, and a large lamp output provides an increased oxidation decomposition rate. The lamp output may arbitrarily be selected in accordance with the desired oxidation decomposition rate.

Figure 6:
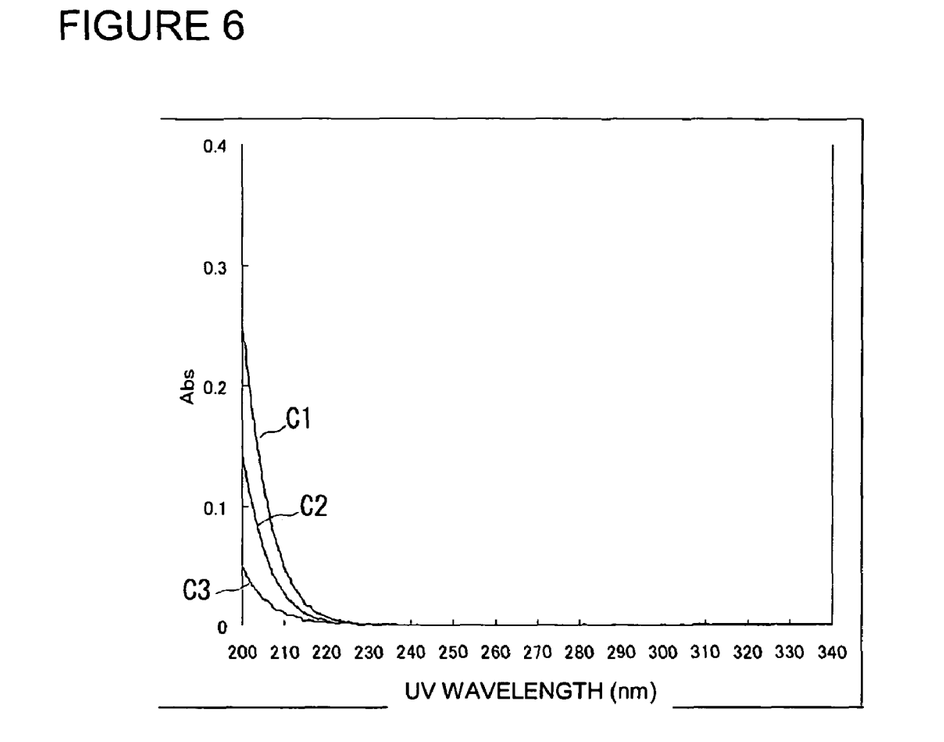
FIG. 6 A graph showing change in $N_2O$ concentration in water under irradiation with an ozone-less high pressure mercury lamp.

FIG. 6 is a graph showing absorption spectra of a nitrous oxide aqueous solution (nitrous oxide content of about 1,000 ppm) under UV light irradiation by using the experimental apparatus of FIG. 1. In this case, the container contains no methylene blue. A horizontal axis represents a measurement wavelength region of 200 to 340 nm, and a vertical axis represents an absorbance. Each of curves C1 to C3 represents an absorbance of nitrous oxide ($N_2O$). C3 represents an absorbance after an irradiation time of 3 min, C2 represents an absorbance after 1 min, and C1 represents an absorbance in the absence of irradiation. The graph revealed that the absorbance was zero with light having a wavelength of 240 nm or more and the light was not absorbed at all. That is, it was revealed that dissociation of nitrous oxide by light energy irradiation was not conducted.

Table 1 shows a change in nitrous oxide concentration determined from the absorbance at a wavelength of 205 nm of FIG. 6. Note that the nitrous oxide concentration was calculated by multiplying a concentration at an irradiation time of 0 as a saturated concentration (value at a water temperature of 25° C.) by a relative value of each absorbance. The results revealed that the nitrous oxide concentration was significantly reduced after irradiation for 3 min.

TABLE 1

Change in $N_2O$ concentration obtained from absorbance at $\lambda$ = 205 nm

| Irradiation time | Absorbance (Relative value) | $N_2O$ concentration * |
|---|---|---|
| 0 min | 0.11855 (100.0%) | 1068 ppm |
| 1 min | 0.06427 (54.2%) | 579 ppm |
| 3 min | 0.02227 (18.8%) | 201 ppm |

* Calculated by multiplying concentration at 0 min as saturated concentration (determined through calculation at water temperature of 25° C.) by relative value of each absorbance.

From the experimental results shown in FIG. 6, substantially no by-product of ozone ($O_3$) was detected. That is, a maximum wavelength ($\lambda$max) of ozone is 260 nm, but the absorbance at 260 nm was at detection limit or less.

<Oxidation of Silicon Wafer>

Figure 7:
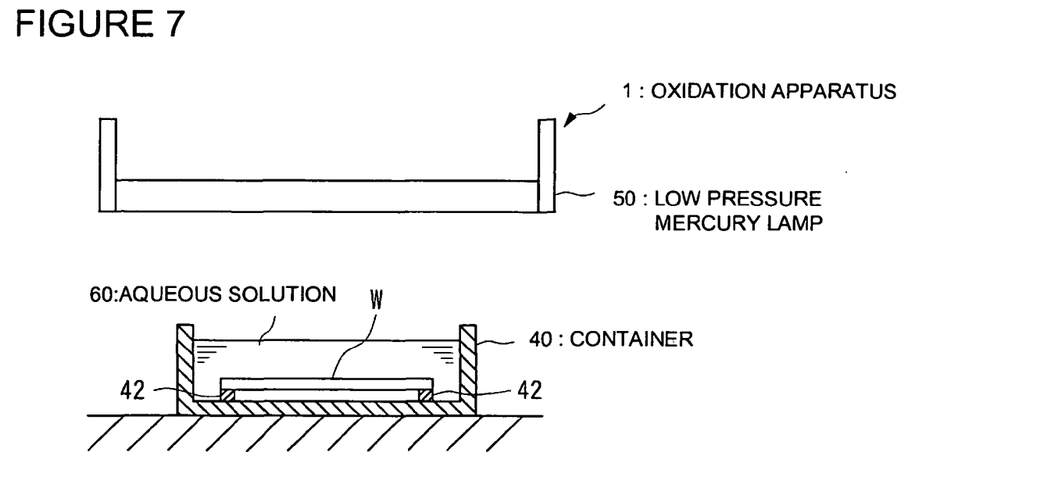
FIG. 7 A schematic diagram of an oxidation apparatus for conducting an oxidation experiment of a silicon wafer.

Next, experimental results of oxidation of a silicon wafer will be described. FIG. 7 is a schematic diagram of an oxidation apparatus for conducting oxidation of a silicon wafer. An oxidation apparatus 1 includes a container 40, and a low pressure mercury lamp 50 arranged directly above the container 40. The low pressure mercury lamp 50 emits light including a wavelength of 240 nm or less and has an output of 110 W. Preferably, the low pressure mercury lamp 50 is arranged as close as possible to the container 40 such that light of the lamp irradiates all surfaces of the container 40.

The container 40 includes side surfaces, a bottom surface, and an open upper surface, and is formed of Teflon®, for example. Protrusions 42 each having a certain height are formed on the bottom surface of the container 40, and a back surface of a silicon wafer W is supported by the protrusions 42. An aqueous solution 60 containing nitrous oxide to be filled in the container 40 contains about 0.1 (1,068 ppm) of nitrous oxide. The silicon wafer W is arranged in the container 40, and then the nitrous oxide aqueous solution 60 is filled in the container 40 such that the silicon wafer W is entirely and sufficiently immersed. In this example, as a silicon wafer to be oxidized, an oxide present on its surface has removed with a hydrogen fluoride aqueous solution in advance is used.

Figure 8:
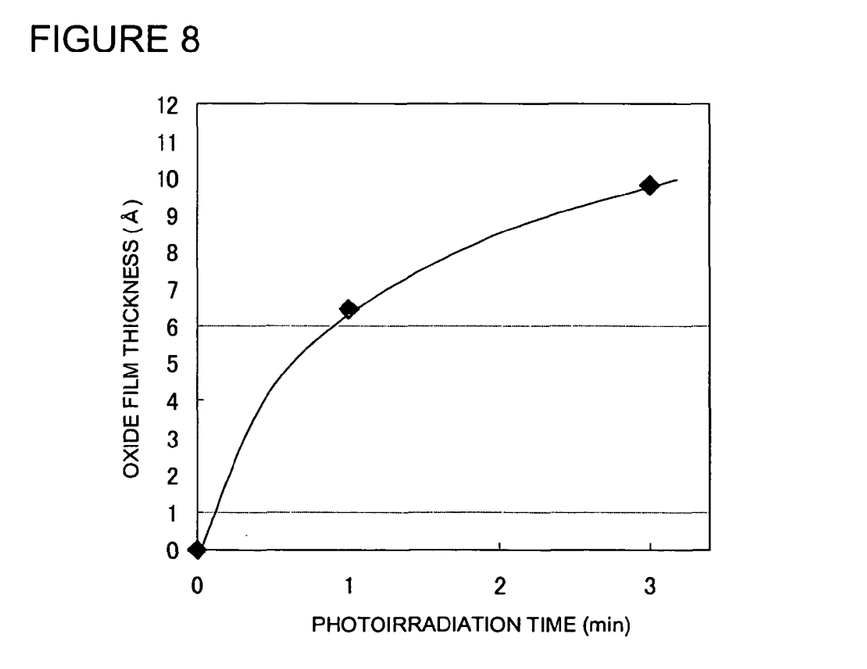
FIG. 8 A graph showing experimental results of oxidation of a silicon wafer obtained by using the experimental apparatus of FIG. 7.

FIG. 8 is a graph showing results of oxidation of a silicon wafer obtained by using the oxidation apparatus shown in FIG. 7, and shows a relationship between photoirradiation time represented by a horizontal axis and thickness (Å) of an oxide film formed on a silicon wafer surface represented by a vertical axis. The thickness of the oxide film was determined through waveform analysis of Si2p spectrum through X-ray photoelectron spectroscopy (XPS). This method is described in Kazuaki Okuda, Akio Ito, "Measurement of a thickness of a thin metal surface oxide film by X-ray photoelectron spectroscopy", Bunseki Kagaku, vol. 40, (1991), pp. 691-696. The graph of FIG. 8 confirmed that an oxide film with a thickness of about 6 Å was formed after a photoirradiation time of 1 min, and an oxide film with a thickness of about 10 Å was formed after a photoirradiation time of 3 min.

Figure 9:
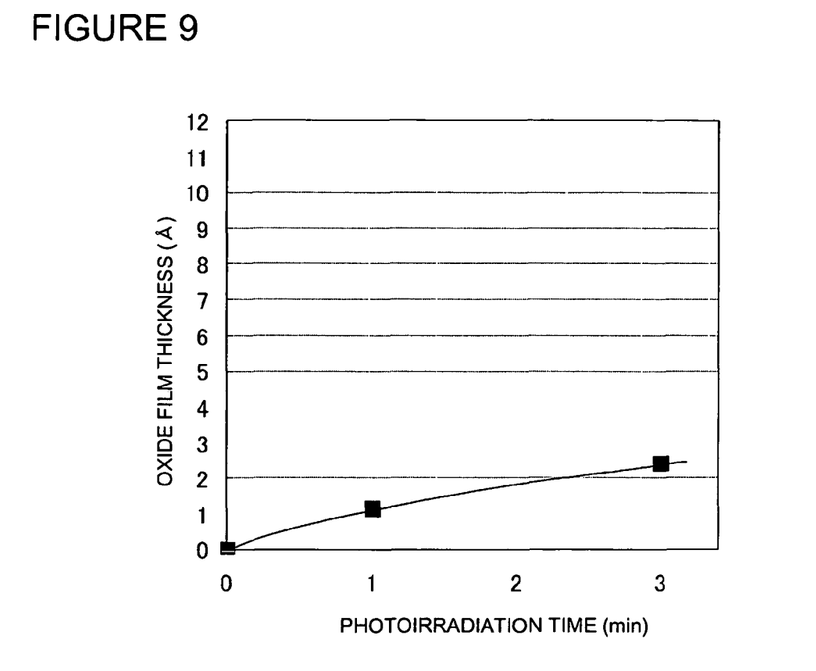
FIG. 9 A graph showing experimental results of oxidation of a silicon wafer obtained by using the experimental apparatus of FIG. 7 in the case where water containing helium (He) dissolved therein is used.

FIG. 9 is a graph showing a relationship between photoirradiation time and thickness of an oxide film formed on a silicon wafer surface by using the oxidation apparatus shown in FIG. 7 in the case where the silicon wafer W has been oxidized using water (helium content of about 16 ppm) containing helium (He) dissolved therein. For comparison with nitrous oxide-dissolved water, helium was forcibly dissolved in the water for removing air components (such as $N_2$, $O_2$, and $CO_2$) dissolved in the water to be used. The graph of FIG. 9 revealed that an oxide film with a thickness of only about 1 Å was formed after an irradiation time of 1 min and an oxide film with a thickness of only about 2 Å was formed after an irradiation time of 3 min. Comparison with FIG. 8 confirmed that the oxide film can efficiently be formed on the surface of the silicon wafer W brought into contact with the water by irradiating nitrous oxide in the water with light.

The oxidation (shown in FIG. 8 or 9) of the silicon wafer was all conducted at room temperature (about 24° C.). In the oxidation, the low pressure mercury lamp 50 was used as a light source for dissociating nitrous oxide, but a light source excluding the low pressure mercury lamp can be used as long as the light source emits light having a wavelength of 240 nm or less. The lamp output may arbitrarily be changed and may have an output excluding 110 W for realizing oxidation decomposition. In the case where the same lamp is used, an oxidation decomposition rate is generally affected by the output. That is, a small lamp output provides a reduced oxidation decomposition rate, and a large lamp output provides an increased oxidation decomposition rate. The lamp output may arbitrarily be selected in accordance with the desired oxidation decomposition rate.

Figure 10:
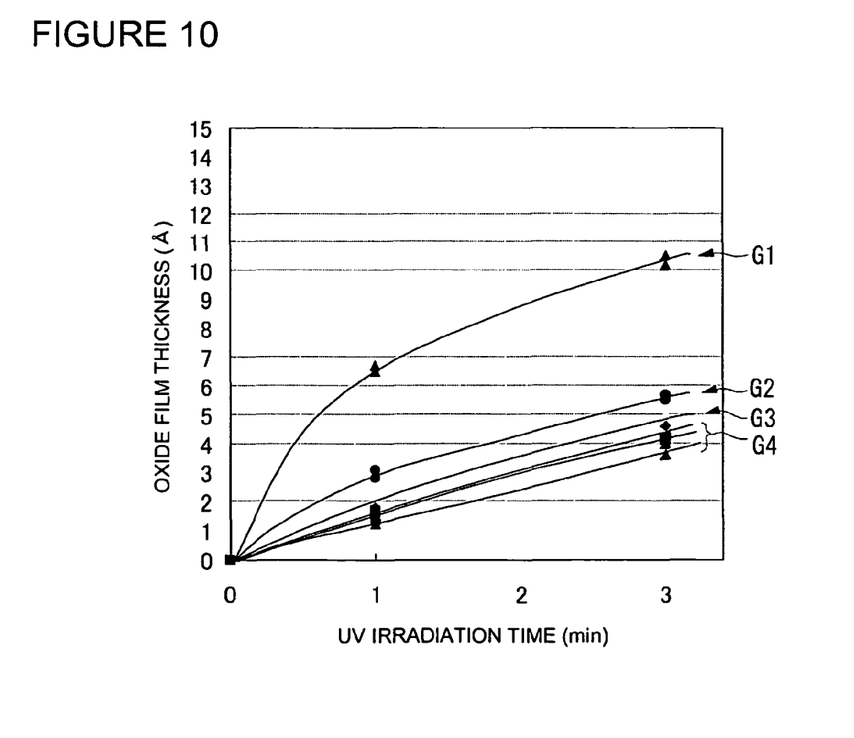
FIG. 10 A graph showing a behavior in silicon oxidation in water containing various gases dissolved therein under irradiation with an ozone-less high pressure mercury lamp.

FIG. 10 is a graph showing a behavior of the oxide film on the silicon wafer W by using the oxidation apparatus of FIG. 7 in the case where an aqueous solution containing various gases dissolved therein was used. A horizontal axis represents UV light irradiation time (min), and a vertical axis represents oxide film thickness (Å). An ozone-less high pressure mercury lamp was used as a light source.

In the graph, G1, G2, G3, and G4 are solutions containing $N_2O$, $O_2$, air, and an inert gas (such as He, $N_2$, or Ar), respectively. The graph revealed that $N_2O$-dissolved water has a significantly higher oxidation rate than those of the other kinds of gas-dissolved water. The thickness of the oxide film after an irradiation time of 1 min was 6 Å for $N_2O$, 3 Å for $O_2$, 2 Å for air, and 1 to 2 Å for He, $N_2$, or Ar.

One factor for reduction in oxidation rate curve with irradiation time is reduction in concentration of an oxidation active species present in water. Thus, injection of unused nitrous oxide into the container 40 for preventing reduction in concentration of the oxidation active species in water presumably suppresses reduction in oxidation rate.

Figure 11:
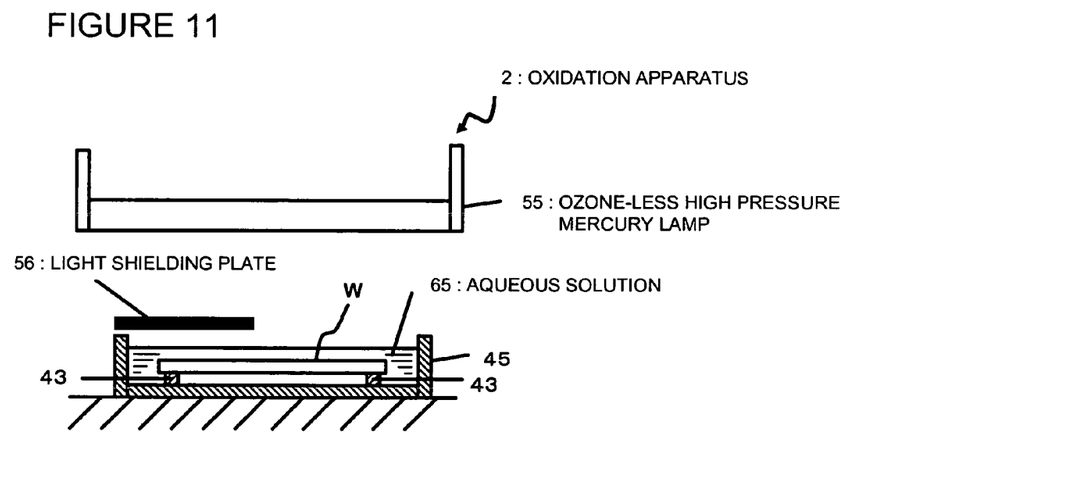
FIG. 11 A schematic diagram of an oxidation apparatus for conducting an oxidation experiment of a silicon wafer in the presence or absence of photoirradiation.

Next, experimental results of silicon wafer oxidation by using an aqueous solution containing nitrous oxide, a hydrogen peroxide solution, and ozone water in the case where a region subjected to photoirradiation and a region subjected to no photoirradiation were provided will be described. FIG. 11 is a schematic diagram of an oxidation apparatus for conducting oxidation of a silicon wafer. An oxidation apparatus 2 includes a container 45, an ozone-less high pressure mercury lamp 55 arranged directly above the container 45, and a light shielding plate 56 for shielding photoirradiation of a defined region of the silicon wafer. The ozone-less high pressure mercury lamp 55 emits light including a wavelength of 240 nm or less. This example shows a case where the light shielding plate 56 was arranged above an aqueous solution 65 as shown in FIG. 11, but the light shielding plate 56 only needs to shield light to be irradiated to the aqueous solution in contact with a substrate. Thus, the light shielding plate 56 may be arranged in the aqueous solution 65, or the light shielding plate 56 may be arranged in contact with the substrate. Oxidation of the substrate in the present invention provides no light energy to the substrate directly and provides light energy to nitrous oxide in the solution in contact with the substrate. Thus, light does not necessarily have to reach a substrate surface, and the aqueous solution in contact with the substrate may be irradiated with light horizontally such that no light is directly irradiated to the substrate surface to dissociate nitrous oxide and oxidize the substrate, for example. In this case, the light shielding plate may be arranged on a side of the substrate for shielding light. In any case, the present invention is realized even if light eventually reaches the substrate surface as long as no chemical reaction suppressing oxidation occurs on the surface of the substrate itself.

The container 45 includes side surfaces, a bottom surface, and an open upper surface, and is formed of Teflon®, for example. Protrusions 43 each having a certain height are formed on the bottom surface of the container 45, and a back surface of the silicon wafer W is supported by the protrusions 43. An aqueous solution 65 to be filled in the container 45 is an aqueous solution containing about 0.1% of nitrous oxide, a 31% hydrogen peroxide solution, or 4 ppm ozone water. The silicon wafer W is arranged in the container 45, and then the aqueous solution 65 is filled in the container 45 such that the silicon wafer W is entirely and sufficiently immersed. Then, the light shielding plate 56 is arranged above the aqueous solution 65 so as to partly cover the silicon wafer. In this example, as a silicon wafer to be oxidized, an oxide on its surface has removed with a hydrogen fluoride aqueous solution in advance is used, and all oxidation treatments are conducted in room temperature for 1 min.

The thickness of the oxide film on the silicon wafer W immersed in about 0.1% $N_2O$-dissolved water was 4.5 Å in a region subjected to photoirradiation. However, the thickness thereof was a detection limit (0.1 Å) or less in a region subjected to no photoirradiation, and oxidation did not proceed at all. The thickness of the oxide film in the 31% hydrogen peroxide solution was 3.7 Å in the region subjected to photoirradiation and 2.7 Å in the region subjected to no photoirradiation. The thickness of the oxide film in the 4 ppm ozone water was 1.9 Å in the region subjected to photoirradiation and 3.2 Å in the region subjected to no photoirradiation. That is, ratios of the oxide film thickness in the region subjected to photoirradiation to the oxide film thickness in the region subjected to no photoirradiation were 45 times or more with about 0.1% $N_2O$-dissolved water, 1.4 times with 31% hydrogen peroxide solution, and 0.6 time with 4 ppm ozone water. With the ozone water, the oxide film thickness reduced in the region subjected to photoirradiation. The results confirmed that a difference in oxidizing power between the region subjected to photoirradiation and the region subjected to no photoirradiation was very large with the $N_2O$-dissolved water compared to that with the hydrogen peroxide solution or the ozone water, and that silicon in the region subjected to photoirradiation alone can be oxidized by controlling the photoirradiation region without oxidizing the region subjected to no photoirradiation.

Next, a silicon wafer oxidation experiment employing an excimer lamp as a light source will be described. The used excimer lamp emits light having a wavelength of 172 nm, but use of the excimer lamp in an atmosphere causes extensive ozone generation. That is, light is absorbed by the atmosphere. Thus, photoirradiation was conducted while a nitrogen gas was purged for preventing light attenuation by the atmosphere.

Photoirradiation was conducted for 1 min during purging of about 5 min under experimental conditions including: an inner volume of a chamber of 8 l; a nitrogen flow rate of 12 l/min; a water temperature of 23° C.; a water amount of 50 ml; and a distance between the excimer lamp and the container of 3 mm. Three types of aqueous solutions used for the experiment include a helium aqueous solution (helium content of about 16 ppm), a nitrous oxide aqueous solution (nitrous oxide content of about 1,000 ppm), an oxygen aqueous solution (oxygen content of about 40 ppm).

The thickness of the oxide film on the silicon wafer W immersed in the helium aqueous solution was 0.4 Å. The oxide film thickness was 0.3 Å with the nitrous oxide aqueous solution, and the oxide film thickness was 0.5 Å with the oxygen aqueous solution. The results confirmed that oxidation hardly proceeded with all aqueous solutions. Further, the thickness of the oxide film did not change even in the case where the irradiation time was extended for 3 min with respect to the nitrous oxide aqueous solution.

Photoirradiation was conducted while droplets (of 0.2 ml) were placed on the silicon wafer and the droplets were in contact with the excimer lamp. Photo irradiation was conducted under purging of a nitrogen gas in the same manner as that described above. The results confirmed that the oxide film thickness was 0.6 Å with the nitrous oxide aqueous solution and the oxide film thickness was 0.4 Å with the oxygen aqueous solution and that oxidation hardly proceeded with both aqueous solutions.

The experimental results suggested that: light (172 nm) emitted from the excimer lamp was mostly absorbed by water; nitrous oxide was hardly decomposed; and the oxide film hardly grew on the surface of the silicon wafer. A maximum absorbance of water is at a wavelength of 167 nm, and thus light to be irradiated to the aqueous solution must have a wavelength longer than a wavelength at which the absorbance of water is sufficiently small. At the same time, the absorbance of light by nitrous oxide must be shorter than 240 nm. In this way, a desired wavelength range of light to be irradiated to the nitrous oxide aqueous solution is 173 nm or more and 240 nm or less.

In the oxidation apparatus 1 shown in FIG. 7, distances between the low pressure mercury lamp 50 and the container 40, and between the low pressure mercury lamp 50 and the silicon wafer W are not particularly defined. In the case where the same light source is used, a small distance between the light source and nitrous oxide existing in an adjacent to an oxidation target substance very closely generally allows efficient dissociation of nitrous oxide with increased illuminance and increases an oxidation rate of the oxidation target substance. In contrast, a large distance between the light source and nitrous oxide existing in an adjacent to the oxidation target substance very closed degrades efficient dissociation of nitrous oxide with reduced illuminance and reduces the oxidation rate of the oxidation target substance. The above-mentioned distance may be changed in accordance with the desired oxidation rate of a substrate.

<Aluminum Oxidation>

Next, experimental results of oxidation of an aluminum plate by using an aqueous solution containing nitrous oxide, a hydrogen peroxide solution, and ozone water in the case where a region subjected to photoirradiation and a region subjected to no photoirradiation are provided will be described. The experiment was conducted by changing the silicon wafer W of the oxidation apparatus 2 shown in FIG. 11 to the aluminum plate.

The container 45 includes the side surfaces, the bottom surface, and the open upper surface, and is formed of Teflon®, for example. The protrusions 43 each having a certain height are formed on the bottom surface of the container 45, and the back surface of the aluminum plate is supported by the protrusions 43. The aqueous solution 65 to be filled in the container 45 is an aqueous solution containing about 0.1% of nitrous oxide, a 31% hydrogen peroxide solution, or 4 ppm ozone water. The aluminum plate is arranged in the container 45, and then the aqueous solution 65 is filled in the container 45 such that the aluminum plate is entirely and sufficiently immersed. The light shielding plate 56 is arranged above the aqueous solution so as to partly cover the aluminum plate. In this example, for confirming reproducibility of experimental data, the aluminum plate to be oxidized had a thickness of a natural oxide film on the surface of the aluminum plate before oxidation treatment of about 17 Å through pretreatment with a phosphoric acid aqueous solution. All oxidation treatments were conducted in room temperature for 1 min. The effect of the oxidation treatments was confirmed by oxide film thickness increase with respect to the natural oxide film thickness.

The oxide film thickness increase of the aluminum plate immersed in about 0.1% $N_2O$-dissolved water was 10.9 Å in a region subjected to photoirradiation. However, the thickness thereof was a detection limit (1.4 Å) or less in a region subjected to no photoirradiation, and oxidation did not proceed at all. The oxide film thickness increase in 31% hydrogen peroxide solution was 2.5 Å in the region subjected to photoirradiation and 1.8 Å in the region subjected to no photoirradiation. The oxide film thickness increase in 4 ppm ozone water was 10.4 Å in the region subjected to photoirradiation and 2.7 Å in the region subjected to no photoirradiation. That is, ratios of the oxide film thickness increase in the region subjected to photoirradiation to the oxide film thickness increase in the region subjected to no photoirradiation were 7.8 times or more with about 0.1% $N_2O$-dissolved water, 1.4 times with 31% hydrogen peroxide solution, and 3.9 times with 4 ppm ozone water. The results confirmed that a difference in oxidizing power between the region subjected to photoirradiation and the region subjected to no photoirradiation was very large with the $N_2O$-dissolved water compared to that with the hydrogen peroxide solution or the ozone water, and that aluminum in the region subjected to photoirradiation alone can be oxidized by controlling the photoirradiation region without oxidizing the region subjected to no photoirradiation.

The preferred examples of the present invention are described in detail. However, the present invention is not limited to such specific examples, and various modifications and changes may be made within a range of a gist of the present invention described in claims.

The examples described the experiments of oxidation of the silicon wafer and the aluminum plate. The results confirmed that the present invention can also be applied to local oxidation of a substrate excluding the silicon wafer and the aluminum plate. The selectively formed oxidized region may obviously serve as a selected insulating region of a substrate of a conductive material, an etching protective film (mask) pattern with excellent chemical resistance, or a pattern of an ornament, similar to the oxidized region formed by the conventional method.

The nitrous oxide aqueous solution to be used for oxidation had an $N_2O$ concentration of about 0.1% in the examples, but the $N_2O$ concentration is not limited thereto. For obtaining a certain effect, the $N_2O$ concentration must be 10 ppm or more. A high concentration leads to an increased oxidation rate, but in consideration of effects of concentration change due to generation of bubbles or dissipation of $N_2O$ into an atmosphere under photoirradiation at an atmospheric pressure, the concentration is preferably 5,000 ppm or less, more preferably 100 ppm to 4,000 ppm, and most preferably 500 ppm to 3,000 ppm.

A method of controlling the photoirradiation region is not particularly limited. Examples of the method include: a method of arranging a mask (reticle) for shielding irradiation of selected light above a solution containing nitrous oxide ($N_2O$) in which a substrate is immersed; and a method of irradiating the target region alone with collected narrow light, laser light, or the like while moving the light, similarly to general photolithography. Use of those methods of controlling the photoirradiation region allows direct and selective oxidation of the desired region without a photolithography step employing a resist.

The nitrous oxide aqueous solution may contain other oxygen-containing precursors in water as long as a function of generating dissociated atomic oxygen (O) under photoirradiation is not inhibited. For example, $O_2$ and the like may be mixed as described referring to FIG. 10.

INDUSTRIAL APPLICABILITY

The present invention relates to a method of oxidizing a substance and an oxidation apparatus therefor, and the present invention has wide industrial applicability. For example, the present invention may be used for: oxidation of a silicon wafer, another compound semiconductor substrate, a circuit substrate, or the like; sterilization, disinfection, surface treatment, deodorization, and discoloring of a substance such as a metal or a resin; decomposition of a toxic organic substance (such as trihalomethane or dioxin); and the like. Further, the present invention allows reaction control by controlling the presence or absence of UV light irradiation or controlling UV light irradiation positions, and thus can be used for an oxidation reaction of a substance in a liquid by using a microreactor or the like.

The invention claimed is:

1. A method of oxidizing a substance, characterized by comprising:
   bringing a substance into contact with a solution containing nitrous oxide ($N_2O$);
   irradiating the solution with UV light, wherein the UV light irradiated has a wavelength of 173 nm to 240 nm, so as to oxidize said substance; and
   controlling a time period of the oxidizing the substance based on a time period of the irradiating the UV light,
   wherein a solvent of said solution is selected from the group consisting of water, methanol, ethanol, isopropanol, methylcyclohexane, cyclohexane, acetonitrile, hexane, dioxane, glycerine, n-pentane and dichloromethane.

2. A method of oxidizing a substance according to claim 1, wherein:
   the solution is an aqueous solution containing nitrous oxide dissolved therein.

3. A method of oxidizing a substance according to claim 2, further comprising controlling a UV light irradiation region.

4. A method of oxidizing a substance according to claim 3, wherein the substance is a semiconductor substrate.

5. A method of oxidizing a substance according to claim 2, wherein the substance is one kind of substance selected from the group consisting of silicon, aluminum, copper, iron, zinc, titanium, tantalum, silver, zirconium, tungsten, chromium, molybdenum, nickel, hafnium, ruthenium, niobium, yttrium, scandium, neodymium, lanthanum, cerium, cobalt, vanadium, manganese, gallium, germanium, indium, tin, rhodium, palladium, cadmium, antimony, and alloys including them.

6. A method of oxidizing a substance according to claim 1, further comprising controlling a UV light irradiation region.

7. A method of oxidizing a substance according to claim 1, further comprising bringing the substance into contact with the solution by immersing the substance in the solution.

8. A method of oxidizing a substance according to claim 1, further comprising bringing the substance into contact with the solution by dissolving the substance in the solution.

9. A method of oxidizing a substance according to claim 1, further comprising bringing the substance into contact with droplets of the solution.

10. A method of oxidizing a substance according to claim 9, further comprising bringing the substance into contact with the solution by dropping the solution on the substance to be rotated.

11. A method of oxidizing a substance according to claim 1, further comprising arranging a mask for shielding UV light irradiation above the substance.

12. A method of oxidizing a substance according to claim 1, wherein the UV light is convergent light.

13. A method of oxidizing a substance according to claim 1, wherein the substance is one kind of substance selected from the group consisting of silicon, aluminum, copper, iron, zinc, titanium, tantalum, silver, zirconium, tungsten, chromium, molybdenum, nickel, hafnium, ruthenium, niobium, yttrium, scandium, neodymium, lanthanum, cerium, cobalt, vanadium, manganese, gallium, germanium, indium, tin, rhodium, palladium, cadmium, antimony, and alloys including them.

14. A method of oxidizing a substance according to claim 1, wherein the substance is a semiconductor substrate.

15. A method of oxidizing a substance according to claim 1, further comprising irradiating the solution with the UV light in an inert gas atmosphere.

16. A method of oxidizing a substance according to claim 1, further comprising irradiating the solution with the UV light in a vacuum atmosphere.

17. A method of oxidizing a substance according to claim 1, further comprising conducting oxidation by arranging a light source and the substance in the solution.

18. A method of oxidizing a substance according to claim 1, wherein a concentration of the nitrous oxide in the solution is 10 ppm to 5,000 ppm.

19. A method of oxidizing a substance according to claim 1, wherein said solution contains the nitrous oxide dissolved in the solvent having an ability of transmitting light of a wavelength of 240 nm or less.

20. A method of oxidizing of a substance according to claim 1, wherein a selected region of said substance is not oxidized, by not allowing the UV light irradiation to said selected region.

* * * * *